United States Patent [19]

Bone et al.

[11] Patent Number: 5,045,314

[45] Date of Patent: Sep. 3, 1991

[54] **CONTROL OF PARASITIC NEMATODE OVA/LARVAE WITH A *BACILLUS LATEROSPORUS***

[75] Inventors: Leon W. Bone, Auburn, Ala.; Samuel Singer, Macomb, Ill.

[73] Assignee: The United States of America as represented by the Secretary of Agriculture, Washington, D.C.

[21] Appl. No.: 436,154

[22] Filed: Nov. 14, 1989

[51] Int. Cl.$^5$ ..................... A01N 63/02; A61K 35/74; A61K 37/02

[52] U.S. Cl. ......................................... 424/93; 424/92; 514/2; 514/21; 514/12; 530/300; 530/324; 435/822

[58] Field of Search ..................... 424/92, 93; 500/300, 500/224; 514/2, 21, 12; 435/822

[56] References Cited

U.S. PATENT DOCUMENTS 4,781,922 11/1988 Bone ..................................... 424/92

OTHER PUBLICATIONS

H. Ciordia et al., "A Preliminary Report on the Effects of *Bacillus thuringiensis* var. thuringiensis Berliner on the Development of the Free-Living Stages of Some Cattle Nematodes," J. Parasitol. 47:41 (Aug. 1961).

Kurt P. Bottjer et al., "Nematoda: Susceptibility of the Egg to *Bacillus thuringiensis* Toxins," Exper. Parasitol 60: 239–244 (1985).

Leon W. Bone et al., "Trichostrongylus colubriformis: Larvicidal Activity of Toxic Extracts from *Bacillus sphaericus* (Strain 1593) Spores," Exper. Parasitol 64: 514–516 (1987).

Montgomery E. Favret et al., "Insecticidal Activity of *Bacillus laterosporus*," J. Invertebr. Pathol. 45: 195–203 (1985).

*Primary Examiner*—Howard E. Schain
*Attorney, Agent, or Firm*—M. Howard Silverstein; Curtis P. Ribando; John D. Fado

[57] ABSTRACT

Nematodes are controlled in host animals by contacting the animal or its environment with a bacterial toxin produced by strains of *Bacillus laterosporus*, the toxin being capable of inhibiting nematode egg hatchability and/or larval development.

10 Claims, No Drawings

CONTROL OF PARASITIC NEMATODE OVA/LARVAE WITH A *BACILLUS LATEROSPORUS*

BACKGROUND OF THE INVENTION

1. Field of the Invention

Typically, high concentrations of anthelmintic compounds are required for killing parasites in their habitat within a host. In the case of intestinal nematodes, anthelmintics must be ingested or absorbed by the worms for expulsion of the parasite from the host. The absorption of the anthelmintic compound by the nematode within the host does not necessarily result in ovicidal activity. Animals being treated are placed in a different pasture or area than before treatment to avoid nematodal ova. There is a need for products which control nematodal ova in the environment of the animal.

This invention relates to a method of controlling nematodes by contacting the eggs and larvae thereof with a bacterial toxin having ovicidal and larvicidal activity.

2. Description of the Prior Art

Luthy et al. [Pharmacol. Therapeut. 13: 257–283 (1981)] teach that various Bacillus species have been recognized as insecticidal pathogens, with *Bacillus thuringiensis* being the most widely used, commercially available bacterium for insect control. According to Burgess [Parasitol. 84: 79–117 (1982)] a number of isolates of *B. thuringiensis* have been reported. Some of the earlier bacterial varieties were active against lepidopteran insects, more recent isolates of *B. thuringiensis* show activity toward nonlepidopteran insect species. For example, *B.t. israelensis* is active against dipteran insects, such as mosquito species and blackfly larvae. Other varieties of *B. thuringiensis* also show promise against mosquito species which play an important role in the transmission of parasitic diseases of man. Favret et al. [J. Invertebr. Pathol. 45: 195–203 (1985)] suggest that a heat-resistant toxin from *B. laterosporus* is pathogenic to mosquito larvae. They also report that this pathogenicity is associated with the cell mass rather than the culture supernatant or bacterial spores.

Despite the use of microbial species and their products as insecticides, there is not much information available about the microbial control of nematodes. Ciordia et al. [J. Parasitol. 47: Abstract 41 (1961)] describe the mixing of spores of *B. thuringiensis* with cow feces that contain eggs of *Cooperia punctata, C. oncophora,* and *Ostertagia ostertagi* and recover reduced numbers of third-stage larvae as the concentration of spores per gram of feces increased clearly showing that some strains of *B. thuringiensis* have nematicidal activity.

Bottjer et al. [Exper. Parasitol. 60: 239–244 (1985)] teach that a large number of strains of *B. thuringiensis* and their toxins were effective in killing the ruminant nematode *Trichostrongylus colubriformis* and other nematodes. All the tests strains of *B. thuringiensis* were toxic to *T. colubriformis* eggs. In U.S. Pat. No. 4,781,922, Bone discloses a method of controlling nematodes in host animals with a toxin from *B. sphaericus* having ovicidal activity.

SUMMARY OF THE INVENTION

We have now surprisingly discovered that spores of selected strains of *B. laterosporus* contain a compound or compounds that inhibit egg hatching and/or larval development of an animal-parasitic nematode (roundworm). This activity is completely unexpected because nematicidal activity has not been reported for *B. laterosporus,* and the ovicidal/larvicidal activity in the selected strains is unrelated to published accounts of insecticidal activity in the same strains, indicating that different toxins are involved. In a typical application of the invention, a sporal extract of the bacterium is combined with a carrier and spread throughout the animal's environment in a manner effective to promote its ovicidal activity.

In accordance with this invention, it is an object of the invention to provide an agent having ovicidal activity against nematodes in a host animal's habitat.

Another object of the present invention is to provide a bacterial preparation comprising a toxin having ovicidal activity.

And yet another object of the present invention is to provide means of enhancing the ovicidal activity of a toxin produced by *B. laterosporus.*

Other objects and advantages of this invention will become readily apparent from the ensuing description.

DEPOSIT OF BIOLOGICAL MATERIAL

Four strains of *B. laterosporus* were deposited on July 14, 1989, under the conditions of the Budapest Treaty, with the Agricultural Research Service Culture Collection in Peoria, Ill. These strains and their corresponding accession numbers are shown below in Table I.

TABLE I

| Name | Strain Designation | NRRL Number |
|---|---|---|
| Bacillus laterosporus | ATCC 64 | B-18520 |
| Bacillus laterosporus | BON 706 | B-18521 |
| Bacillus laterosporus | CCEB 629 | B-18522 |
| Bacillus laterosporus | NRS 1647 | B-18523 |

DETAILED DESCRIPTION OF THE INVENTION

This invention relates to an exogenous method of killing the eggs and larvae of a nematode or inhibiting hatchability of nematode eggs by the distribution of a bacterial toxin to the area where the nematode eggs and larvae are found. Thus, the nematode may be controlled, and infection of noninfected animals and reinfection of host animals avoided.

Selected strains of the bacterium *B. laterosporus* produce a toxin that has the required ovicidal/larvicidal activity. This toxin is characterized by a molecular weight of approximately 2900 daltons and an apparent UV absorbance at 205, 220, and 268 nm. *B. laterosporus* is a well-known bacterium, cultures of which are generally available, such as through recognized depositories. As shown in Table I above, four such strains have been deposited by the applicants in the Agricultural Research Patent Culture Collection in Peoria, Ill. These strains all have characteristics typical of the genus *Bacillus* and the species *laterosporus* as given in Bergey's Manual of Systematic Bacteriology, Vol. 2, Williams & Wilkins, pp. 1104–1139 (1986), herein incorporated by reference. Other strains of *B. laterosporus* which produce the subject 2900-dalton toxin are also useful in accordance with the method of the present invention.

Various preparations comprising the subject toxin may be derived from cultures of the toxin-producing strains of *B. laterosporus.* For example, dried bacterial powders (primary bacterial powders) can be prepared by lyophilizing, or otherwise drying, the solids separated from the whole cell cultures. Alternatively, the toxin may be isolated in substantially pure form from the spores of *B. laterosporus* strains, by HPLC or other conventional methods.

The bacterial toxin may be distributed or spread throughout an animal's environment—pasture, feedlot, barn, etc.—to ensure its contact with nematode ova/larvae. Preferably, it can be combined with a carrier to facilitate the distribution of the product in the infected animal's environment. The toxin, in combination with the carrier, should be in an effective amount to be toxic to the eggs/larvae or inhibit egg hatching under the conditions of administration contemplated by the invention. The carrier may be a liquid which suspends the bacterial product in solution without harmful effects to the toxin for facile spreading or distribution throughout the required area. For example, carriers may be water, water-and-oil emulsions, polyhydric alcohols such as propylene glycol, or lipid materials which may be solid or liquid. Additionally, the carrier may be a dry substance on which the bacterial preparation may be absorbed, such as carbohydrate materials, e.g., starch granules.

The toxin may also be applied directly to the hide or skin of an animal when combined with a suitable carrier in the form of a liquid drench.

It will be understood that the actual amount of toxin administered will vary depending upon the nematode species, and the environmental conditions, specifically the temperature. For purposes of the invention, an "effective amount" or "nematicidally effective amount" is defined to mean those quantities of toxin which will result in a significant mortality rate of a test group as compared to an untreated group. The toxin is stable and substantially heat resistant, showing activity in environmental conditions where the temperature is about 75° C. It is also stable of a pH range of about 4.5 to 9.5. Multiple applications may be required in an area to be treated when environmental temperatures are extremely high. It is believed that the toxin either blocks embryonal development of the nematode, thereby precluding hatching of the eggs, or it inhibits larval development, or it inhibits both egg hatching and larval development.

Chemical agents or adjuvants or physical treatments may be used to increase the ovicidal/larvicidal activity of the toxin. A preferred treatment, heating at about 50°–65° C. for 1–4 hr, significantly enhances toxicity to nematode eggs. Likewise, enzymatic treatment of the microbial spores with lysozyme also enhances toxicity.

The following examples are intended only to further illustrate the invention and are not intended to limit the scope of the invention which is defined by the claims.

EXAMPLE 1

Cultures of each of 27 different strains of *B. laterosporus* were grown on NYSM broth [Favret et al., (supra)], modified so that 2% nutrient broth powder ("Difco") was used rather than 0.8%. Inoculum buildup and preparation of the dried bacterial powders by lyophilization were conducted according to the procedures of Singer [Proc. IIIrd Int. Colloq., Invertebr. Pathol., pp. 485–489 (1982)], herein incorporated by reference. Upon use, the dried bacterial powder was dissolved in reagent grade water (18 M$\Omega$, "Milli-Q"). Total protein/ml was determined for each aqueous preparation by Lowrey's procedure [J. Biol. Chem. 193: 265 (1951)].

The ruminant nematode *T. colubriformis* was maintained in male, crossbred goats that averaged 20 kg in weight at the time of infection. The animals were killed at 21 da after infection, and the eggs were removed from rectal feces, surface-sterilized, and placed in media according to the procedures described by Bottjer et al. (supra).

Ovicidal activity was determined by placing a dose of the dissolved preparation of *B. laterosporus* in the wells of microliter plates that contained nematode eggs (10–30 eggs/well) in *Caenorhabditis briggsae* maintenance media supplied by Gibco, Grand Island, NY. Viability was determined by inverted microscopy after a 24-hour exposure at 22° C. Sixteen replicates were performed for each sample, while unexposed eggs were used as controls to determine the percentage of larval viability.

The results in Table II show that four of the 27 tested strains had nematicidal effects, and that nematicidal activity was not correlated to the insecticidal activity reported by Favret et al., indicating that different toxins are involved.

EXAMPLE 2

Dissolved bacterial preparations derived from *B. laterosporus* strains ATCC 64, Bon 706, CCEB 629, and NRS 1647 as described in Example 1 were treated with 10 $\mu$g/ml lysozyme for 2 hr at 37° C. to examine the effect on enzymatic activation and release of the toxin. Each lysozyme-treated preparation was compared to an untreated control in a larval viability study as described in Example 1. The results are reported in Table III.

EXAMPLE 3

Dissolved bacterial preparations derived from *B. laterosporus* strains ATCC 64, Bon 706, CCEB 629, and NRS 1647 as described in Example 1 at a concentration of 1 mg total protein/ml were heated at 60° C. for the periods of time indicated in Table IV to study the effect on toxin activity. Each heat-treated extract was compared to an untreated control in a larval viability study as described in Example 1. The results are reported in Table IV.

EXAMPLE 4

A dissolved bacterial preparation prepared from *B. laterosporus* strain CCEB 629 as described in Example 1 was heat-treated by the procedure of Example 3 for 1, 1.5, 2, and 3 hr. The treated samples were analyzed in a photo-diode array detector whereupon eluted HPLC fractions were scanned by UV over the range of 200–350 nm. The increase in attenuation at 268 nm with increased heating time correlates with larvicidal activity as shown below in Table V. Based upon an average chromatographic retention time of 11.77 min (range of 11.69–11.89 ml/min) at a flow rate of 1.5 ml/min for the four samples vs standard calibration elution, the molecular weight was determined to be approximately 2900 daltons. The toxin isolated by HPLC was characterized by UV absorbance at 205, 220, and 268 nm.

TABLE II

| Evaluation of *B. laterosporus* Strains for Nematicidal Activity | | | |
|---|---|---|---|
| Strain | Source | Ovicidal toxicity, LD$_{50}$ ($\mu$g total protein/ml) | Insecticidal activity |
| ATCC 64 | A | 0.24 | — |

TABLE II-continued

Evaluation of *B. laterosporus* Strains for Nematicidal Acitivity

| Strain | Source[a] | Ovicidal toxicity, $LD_{50}$ (μg total protein/ml)[b] | Insecticidal activity[c] |
|---|---|---|---|
| Bon 706 | B | 6.9 | + |
| CCEB 629 | C | 0.67 | − |
| NRS 1647 | A | 0.22 | + |
| ATCC 6457 | A | − | + |
| ATCC 9141 | A | − | + |
| Bon 705 | B | − | + |
| Bon 707 | B | − | + |
| Bon 708 | B | − | − |
| Bon 712 | B | − | − |
| CCEB 342 | C | − | − |
| NRS 340 | D | − | − |
| NRS 590 | A | − | + |
| NRS 661 | D | − | − |
| NRS 882 | D | − | − |
| NRS 1111 | D | − | − |
| NRS 1267 | D | − | + |
| NRS 1338 | D | − | + |
| NRS 1642 | A | − | − |
| NRS 1643 | A | − | − |
| NRS 1644 | A | − | − |
| NRS 1645 | A | − | − |
| NRS 1646 | A | − | − |
| NRS 1648 | A | − | − |
| Shi 3 | E | − | − |
| Shi 4 | E | − | − |
| Shi 5 | E | − | − |

A - American Type Culture Collection, Rockville, MD.
B - G. J. Bonde, Institute of Hygiene, University of Aarhus, Denmark;
C - O. Lysenko, Department of Insect Pathology, Institute of Entomology, CSAV, Flemingova, Nam 2, Prague 6, Czechoslovakia;
D - R. E. Gordon, Rutgers University, New Brunswick, NJ (present address, ATCC, Rockville, MD);
E - H. Shimanuki, Bioenvironmental Bee Laboratory (USDA), Beltsville, MD.
- not detected.
Reported by Favret et al. (supra);
+ determinable amount;
- not determinable.

TABLE III

Effect of Lysozyme Treatment

| Strain[a] | Increase in ovicidal activity (% over control) |
|---|---|
| ATCC 64 | 31.3 |
| Bon 706 | 17.2 |
| CCEB 629 | 22.5 |
| NRS 1647 | 61.4 |

See Table I for source.

TABLE IV

Effect of Heat Treatment

| Strain[a] | Larval viability (% of control) after heating period (hr) 1 | 1.5 | 2 | 3 | 4 |
|---|---|---|---|---|---|
| ATCC 64 | 37.4 | 35.4 | 22.5 | 5.9 | 0 |
| Bon 706 | 70 | 64.2 | 37.9 | 20 | 0 |
| CCEB 629 | 77.1 | 77.7 | 35.8 | 25.7 | 1.2 |
| NRS 1647 | 80.1 | 6.9 | 8.4 | 0 | 0 |

See Table I for source.

TABLE V

Correlation of HPLC Peak Size to Toxin Activity

| | Heating period (hr) 1 | 1.5 | 2 | 3 |
|---|---|---|---|---|
| Attenuation units (268 nm) | 0.011 | 0.014 | 0.017 | 0.02 |
| Larval viability (% of control) | 77.1 | 77.7 | 35.8 | 25.7 |

It is understood that the foregoing detailed description is given merely by way of illustration and that modification and variations may be made therein without departing from the spirit and scope of the invention.

We claim:

1. A preparation comprising a nematicidal toxin recovered from whole cell culture of *Bacillus laterosporus*, which toxin corresponds to the toxin produced in whole cell cultures of *Bacillus laterosporus* strains selected from the group consisting of NRRL Accession Nos. B-18520, B-18521, B-18522, and B-18523, wherein said toxin is characterized by a molecular weight of approximately 2900 daltons and an apparent UV absorbance at 205, 220 and 268 nm.

2. A preparation of claim 1 wherein said preparation has been heat treated.

3. A preparation of claim 1 wherein said preparation has been lysozyme treated.

4. A method for controlling nematodes comprising contacting the ova or larvae of said nematodes with an effective amount of a toxin which corresponds to the toxin produced in whole cell cultures of *Bacillus laterosporus* strains selected from the group consisting of NRRL Accession Nos. B-18520, B-18521, B-18522, and B-18523.

5. A method as described in claim 4, wherein said toxin has been heat treated.

6. A method as described in claim 4, wherein said toxin has been lysozyme treated.

7. A method as described in claim 4 wherein said toxin is a component of a sporal extract of said strains of *Bacillus laterosporus*.

8. A method as described in claim 4 wherein said nematodes are in a host animal.

9. A method as described in claim 4 wherein said nematodes are in the environment of a host animal.

10. A method as described in claim 4 wherein said nematodes ar *Trichostrongylus colubriformis*.

* * * * *